(12) United States Patent
Wijesundara et al.

(10) Patent No.: US 11,577,074 B2
(45) Date of Patent: Feb. 14, 2023

(54) APPARATUS AND METHOD FOR NERVE STIMULATION AND/OR MONITORING

(71) Applicant: Board of Regents, The University of Texas System, Austin, TX (US)

(72) Inventors: Muthu B. J. Wijesundara, Fort Worth, TX (US); Ryan Andrew Landrith, Fort Worth, TX (US); Caleb P. Nothnagle, Arlington, TX (US); Young-tae Kim, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1234 days.

(21) Appl. No.: 16/074,159

(22) PCT Filed: Mar. 9, 2017

(86) PCT No.: PCT/US2017/021516
§ 371 (c)(1),
(2) Date: Jul. 31, 2018

(87) PCT Pub. No.: WO2017/156232
PCT Pub. Date: Sep. 14, 2017

(65) Prior Publication Data
US 2020/0078586 A1 Mar. 12, 2020

Related U.S. Application Data

(60) Provisional application No. 62/306,909, filed on Mar. 11, 2016.

(51) Int. Cl.
*A61N 1/05* (2006.01)
*A61B 5/00* (2006.01)
*A61B 5/24* (2021.01)

(52) U.S. Cl.
CPC .............. *A61N 1/0553* (2013.01); *A61B 5/24* (2021.01); *A61B 5/6877* (2013.01); *A61B 5/6879* (2013.01); *A61B 5/6886* (2013.01)

(58) Field of Classification Search
CPC .......... A61N 1/05; A61N 1/0553; A61B 5/24; A61B 5/6877; A61B 5/6879; A61B 5/6886
See application file for complete search history.

(56) References Cited

U.S. PATENT DOCUMENTS

| 4,969,468 A | * | 11/1990 | Byers | ...................... A61B 5/287 29/829 |
| 6,456,866 B1 | * | 9/2002 | Tyler | ........................ A61B 5/24 600/377 |

(Continued)

FOREIGN PATENT DOCUMENTS

WO 2015109342 A2 7/2015

OTHER PUBLICATIONS

International Search Report and Written Opinion, conducted by the ISA/EP, corresponding to International Application No. PCT/US2017/021516, dated May 15, 2017, 12 pages.

*Primary Examiner* — Christopher A Flory
(74) *Attorney, Agent, or Firm* — John P. Zimmer; Nexsen Pruet, PLLC (57) ABSTRACT

In one aspect, an apparatus for stimulating and/or monitoring a nerve is described herein. In some embodiments, the apparatus comprises a top substrate layer, a bottom substrate layer in facing opposition to the top substrate layer, and a channel disposed between the top substrate layer and the bottom substrate layer. The apparatus further comprises a plurality of electrodes disposed on one or more interior surfaces of the channel. Additionally, the channel is defined by the top substrate layer, the bottom substrate layer, and a retaining wall extending at least partially between the top (Continued)

substrate layer and the bottom substrate layer. The retaining wall retains the nerve within the channel.

20 Claims, 8 Drawing Sheets

(56) References Cited

U.S. PATENT DOCUMENTS

| | | | |
|---|---|---|---|
| 2003/0074039 A1* | 4/2003 | Puskas | A61N 1/056 607/118 |
| 2008/0172116 A1* | 7/2008 | Mrva | A61N 1/0526 607/115 |
| 2015/0174396 A1* | 6/2015 | Fisher | A61N 1/3605 600/377 |
| 2015/0217109 A1 | 8/2015 | Achyuta et al. | |
| 2015/0303831 A1* | 10/2015 | Kwon | H02N 1/08 310/300 |

\* cited by examiner

APPARATUS AND METHOD FOR NERVE STIMULATION AND/OR MONITORING

CROSS REFERENCE TO RELATED APPLICATIONS

This application is the national stage application under 35 U.S.C. § 371 of International Application No. PCT/US2017/021516, filed on Mar. 9, 2017, which claims priority pursuant to 35 U.S.C. § 119(e) to U.S. Provisional Patent Application Ser. No. 62/306,909, filed on Mar. 11, 2016, each of which is hereby incorporated by reference in its entirety.

FIELD

The present disclosure relates broadly to implantable medical devices and, more particularly, to bioelectronics devices for nerve stimulation and/or monitoring (recording).

BACKGROUND

Virtually all physiological functions are regulated by neural activity. Accordingly, in the field of bioelectronics, it is frequently desirable to interface nerves in a living organism with an apparatus or device that may be used to stimulate or monitor the nerves. Unfortunately, some current bioelectronics devices suffer from one or more disadvantages. For example, some existing devices can be used only with large nerve branches and/or must be placed on the cortical brain surface. Such locations within the patient can be associated with the regulation of many different physiological functions. Accordingly, some existing devices can provide inconsistent results and/or obscure specific pathways of neural control. Additionally, some current devices are invasively penetrating of the nerve, suitable for use with only severed nerves, and/or difficult to use with nerves having a small diameter, such as a diameter of less than 500 μm. Therefore, there exists a need for improved bioelectronics devices and methods of stimulating and/or monitoring nerves that overcome one or more of the foregoing deficiencies of previous devices and methods.

SUMMARY

In one aspect, apparatuses for nerve stimulation and/or monitoring are described herein which, in some cases, can provide one or more advantages compared to other apparatuses. For example, in some embodiments, an apparatus described herein is non-penetrating and removable. An apparatus described herein may also be "closeable" or otherwise able to retain or secure an intact (non-severed) nerve, including an intact nerve having a small diameter. Additionally, in some cases, an apparatus described herein can be made by cost-effective microfabrication techniques and can have small and highly reproducible features. Moreover, an apparatus described herein, in some instances, is able to retain and stimulate and/or monitor an intact nerve while also permitting the nerve freedom of motion within the apparatus, thus preventing or reducing mechanical strain on the nerve.

In some embodiments, an apparatus for nerve stimulation and/or monitoring described herein comprises a top substrate layer, a bottom substrate layer in facing opposition to the top substrate layer, and a channel disposed between the top substrate layer and the bottom substrate layer. Additionally, a plurality of electrodes is disposed on one or more interior surfaces of the channel. Further, the channel can be defined by the top substrate layer, the bottom substrate layer, and a retaining wall that extends at least partially between the top substrate layer and the bottom substrate layer. Moreover, this retaining wall can retain the nerve within the channel of the apparatus. The retaining wall may also retain the nerve in contact with the electrodes. In some implementations, the apparatus further comprises a spacer layer disposed between the top substrate layer and the bottom substrate layer.

In another aspect, methods of stimulating and/or monitoring a nerve are described herein. In some embodiments, such a method comprises placing the nerve in the channel of an apparatus described hereinabove. Moreover, the nerve can be placed in contact with the plurality of electrodes of the apparatus. The method can further comprise sending electrical signals from the electrodes to the nerve and/or receiving electrical signals from the nerve to the electrodes. In addition, in some instances, the top substrate layer and the bottom substrate layer of the apparatus define an opening of the channel at a proximal end of the apparatus, and the method further comprises joining the top substrate layer and the bottom substrate layer to close the opening of the channel at the proximal end of the apparatus following placement of the nerve in the channel. Further, in some cases, the nerve is an intact nerve. Moreover, in some embodiments, the apparatus does not penetrate the nerve when the nerve is placed or retained in the channel. Additionally, in some instances, the nerve is a nerve of a living patient, and the method further comprises placing the apparatus within a biological compartment of the patient. In some such embodiments, the apparatus is sealed within the biological compartment of the patient after the nerve is placed in the channel of the apparatus. Further, such a method can also comprise removing the nerve from the apparatus and removing the apparatus from the patient after sealing the apparatus within the biological compartment of the patient. Additionally, in some embodiments, a method described herein further comprises sending and/or receiving electrical signals to and/or from the nerve, including while the nerve is disposed within a channel of an apparatus described herein.

These and other embodiments are described in greater detail in the detailed description which follows.

DETAILED DESCRIPTION

Embodiments described herein can be understood more readily by reference to the following detailed description, examples, and figures. Elements, apparatus, and methods described herein, however, are not limited to the specific embodiments presented in the detailed description, examples, and figures. It should be recognized that these embodiments are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "from 5 to 10" or "5-10" should generally be considered to include the end points 5 and 10.

Further, when the phrase "up to" is used in connection with an amount or quantity, it is to be understood that the amount is at least a detectable amount or quantity. For example, a material present in an amount "up to" a specified amount can be present from a detectable amount and up to and including the specified amount.

I. Apparatuses for Nerve Stimulation and/or Monitoring

In one aspect, apparatuses for nerve stimulation and/or monitoring are described herein. In some embodiments, such an apparatus comprises a top substrate layer, a bottom substrate layer in facing opposition to the top substrate layer, and a channel disposed between the top substrate layer and the bottom substrate layer. Additionally, a plurality of electrodes can be disposed on one or more interior surfaces of the channel. For example, in some embodiments, top electrodes are disposed on an interior surface of the top surface layer, and bottom electrodes are disposed on an interior surface of the bottom substrate layer.

As described further hereinbelow, the channel of the apparatus can be defined by the top substrate layer, the bottom substrate layer, and a retaining wall extending at least partially between the top substrate layer and the bottom substrate layer. Moreover, the retaining wall can be operable to or can be configured to retain or secure the nerve within the channel of the apparatus. The retaining wall can also retain the nerve in contact with the plurality of electrodes. In addition, in some cases, an apparatus described herein further comprises a spacer layer disposed between the top substrate layer and the bottom substrate layer. The height of this spacer layer can at least partially define a height of the channel. Moreover, in some cases, the top substrate layer and/or the bottom substrate layer comprises a recess, cavity, groove, trough, or furrow. Such a recess can have an elongated shape and define an interior surface of the channel. Thus, in some such instances, the channel of the apparatus is defined by the recess of the top substrate layer, the recess of the bottom substrate layer, and the retaining wall.

Specific components and features of apparatuses according to the present disclosure will now be further described with reference to the figures. It is to be understood that the same reference numerals used in differing figures generally correspond to the same features of an apparatus.

Figure 1A:
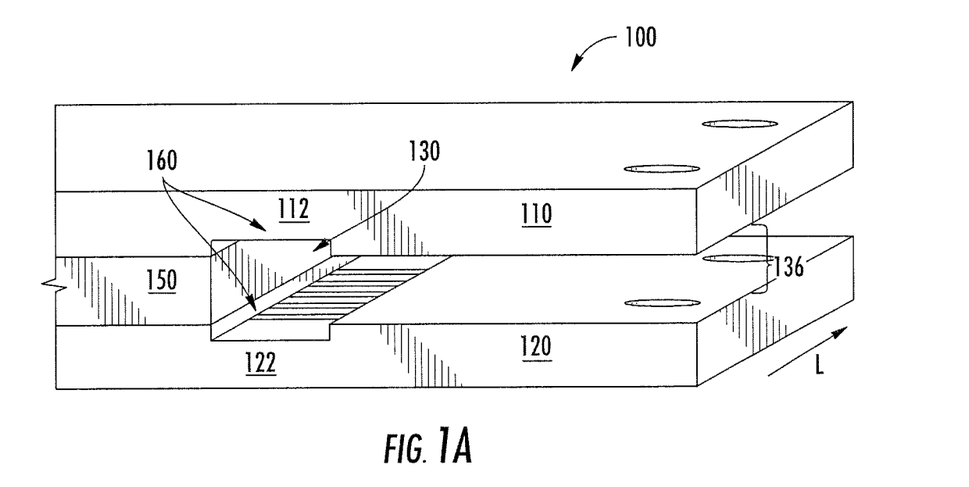
FIG. 1A illustrates a perspective view of an apparatus according to one embodiment described herein.
Figure 1B:
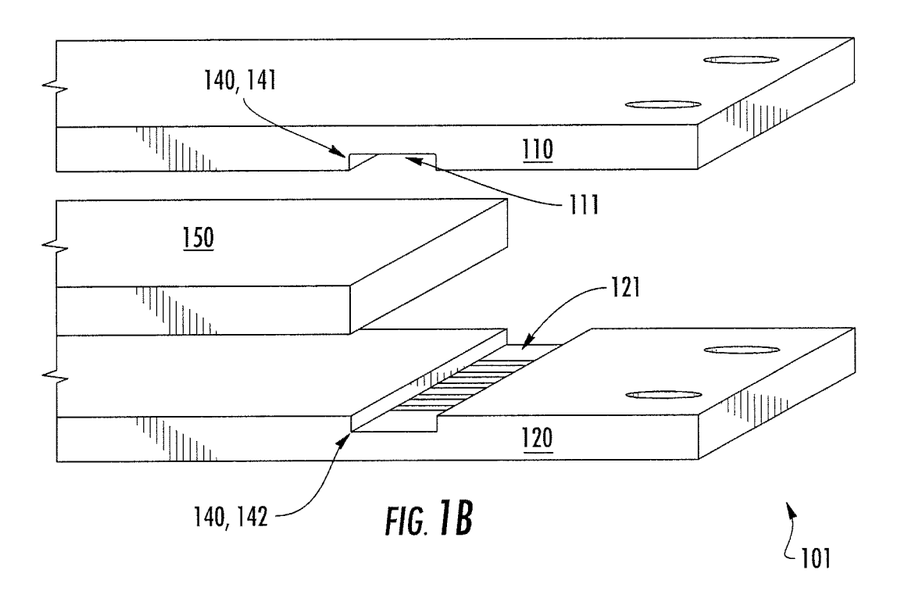
FIG. 1B illustrates an exploded view of the apparatus of FIG. 1A.
Figure 2:
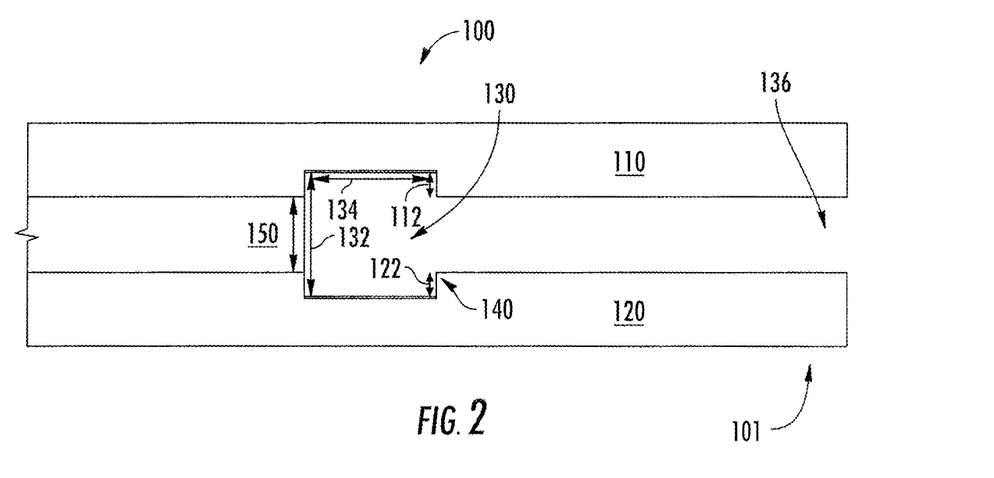
FIG. 2 illustrates a sectional view of the apparatus of FIG. 1A.

FIG. 1A illustrates a perspective view of an apparatus according to one embodiment described herein. FIG. 1B illustrates an exploded view of the apparatus of FIG. 1A. FIG. 2 illustrates a sectional view of the apparatus of FIG. 1A. With reference to FIG. 1A, FIG. 1B, and FIG. 2, an apparatus (100) described herein comprises a top substrate layer (110) and a bottom substrate layer (120). The top substrate layer (110) is in facing opposition to the bottom substrate layer (120). In addition, a channel (130) is disposed between the top substrate layer (110) and the bottom substrate layer (120). The channel (130) is partially defined by the space between the top substrate layer (110) and the bottom substrate layer (120). The channel (130) is also defined by a retaining wall (140) extending partially between the top substrate layer (110) and the bottom substrate layer (120). As illustrated in FIGS. 1A and 1B, the retaining wall (140) can be considered to be a single retaining wall having two discontinuous portions (141, 142). Alternatively, the apparatus (100) can be considered to include two retaining walls (141, 142). This structure is due to the presence of recesses (112, 122) in both the top substrate layer (110) and the bottom substrate layer (120). However, it is also possible for an apparatus described herein to include only one continuous retaining wall (such as only retaining wall portion 142), such as may occur if only one of the top substrate layer and the bottom substrate layer included a recess. In any event, it is to be understood that the retaining wall (140) can be operable to retain a nerve (not shown) within the channel (130).

Further, the apparatus (100) also comprises a spacer layer (150) disposed between the top substrate layer (110) and the bottom substrate layer (120). As described further herein, a height of the spacer layer (150) can at least partially define a height (132) of the channel (130) of the apparatus. Additionally, the spacer layer (150) can bond, attach, or affix the top substrate layer (110) to the bottom substrate layer (120). The spacer layer (150) may be formed separately from the top substrate layer (110) and the bottom substrate layer (120), or it may be incorporated into or formed integrally with the top substrate layer (110) and/or the bottom substrate layer (120). In some instances, though not necessarily in the embodiment illustrated in FIG. 1A, the top substrate layer (110) and the bottom substrate layer (120) may be formed from a single, continuous substrate layer that is folded over upon itself to create the top (110) and bottom (120) substrate layers in facing opposition to each other and separated by the spacer layer (150).

Moreover, in the embodiment of FIG. 1A, the top substrate layer (110) and the bottom substrate layer (120) define an opening (136) of the channel (130) at a proximal end (101) of the apparatus (100). Additionally, the opening (136) of the channel (130) at the proximal end (101) extends along a length (L) of the apparatus (100). The opening (136) can thus permit a nerve (not shown) having a long axis extending generally parallel to the length (L) to be inserted laterally or "sideways" into the channel (130) of the apparatus (100). The retaining wall (140) of the apparatus (100) can then retain the nerve within the channel (130) by partially obstructing the opening (136) of the apparatus (100). For reference purposes herein, the "proximal" end of an apparatus is the end opposite the spacer layer, or, in embodiments lacking a distinct spacer layer, the end opposite an end where the top substrate layer and the bottom substrate layer are joined.

It is to be understood that the height of the retaining wall (140), in conjunction with the height (132) and width (134) of the channel (130), can be selected based on the diameter of the nerve, and can be controlled with sub-micron precision. As used herein, a "height of the retaining wall" refers to the sum of the heights of a plurality of aligned retaining walls or the sum of the heights of any subportions of the retaining wall, when a discontinuous retaining wall or a plurality of collinear or "stacked" retaining walls is used. The nerve, once positioned in the channel (130), may experience movement within the channel (130), such that the apparatus does not penetrate the nerve or otherwise damage the nerve if the apparatus is subjected to movement during movement of muscles or other surrounding tissue. Thus, the apparatus need not be mechanically fastened to the nerve; rather, the nerve can be held inside the apparatus by the retaining wall. Additionally, in some cases, the top substrate layer and the bottom substrate layer of an apparatus can be joined or attached at the proximal end of the apparatus to close the opening of the channel, thereby further retaining or securing a nerve within the channel without damaging the nerve. Thus, an apparatus described herein can be non-penetrating to the nerve. "Penetration" of a nerve, for reference purposes herein, can refer to the nerve's entanglement with or growth into a component of a device, or the piercing of the surface of the nerve by an external component. When penetration occurs, it can be very difficult if not impossible to remove the device without damaging the nerve.

Turning again to the channel (130) of the apparatus (100), the channel (130) has a height (132) and a width (134). The height (132) and width (134) may be approximately equal. As shown in FIG. 2, the height of the retaining wall (140) is less than the height (132) of the channel (130), thus allowing the nerve to be placed in the channel (130) and then to be retained in the channel (130) by the retaining wall (140). The height of the retaining wall (140), in some cases, may equal approximately one-quarter to one-third the height of the channel (130). Additionally, in some instances, the average or maximum height of the channel is less than about 1000 µm, less than about 500 µm, less than about 250 µm, less than about 100 µm, or less than about 50 µm. In some instances, the average or maximum height of the channel is 10-1000 µm, 50-1000 µm, 10-500 µm, 10-300 µm, 10-100 µm, 50-500 µm, 50-300 µm, or 50-100 µm. Further, in some embodiments, the height of the channel is equal to or slightly greater than the diameter of the nerve to be disposed in the channel. The nerve may be any nerve, such as an intact or un-severed small nerve, an organ-modulating nerve fascicle, or a peripheral nerve. In some cases, the nerve may have a diameter of about 25-500 µm, 50-400 µm, 100-300 µm, or 25-200 µm. Other sizes are also possible. Additionally, in some instances, the width of the channel has a value described above for the height of the channel. In some embodiments, for example, the width of the channel is less than 1000 µm, less than 500 µm, less than 250 µm, less than 100 µm, or less than 50 µm.

Further, as described above, the size of the retaining wall used to define the channel of an apparatus described herein can be selected based on the height and/or width of the channel, and/or based on the diameter of the nerve to be disposed in the channel. For example, in some cases, the retaining wall is selected to be low enough to permit insertion of the nerve, but high enough to retain the nerve following insertion. As a non-limiting example of proportions, for an apparatus with a channel height of 600 µm and a channel width of 600 µm, a retaining wall height of 200 µm may be appropriate to retain a nerve having a diameter of 500 to 600 µm. In other cases, the retaining wall height may be less than 200 µm or greater than 200 µm. In some embodiments, the retaining wall height is up to 300 µm. Moreover, as described above, it is to be understood that the height of the retaining wall can be the total height of more than one portion of a discontinuous retaining wall or of a plurality of aligned retaining walls that operate cooperatively to retain a nerve. It is further to be understood that an apparatus having only a single 200 µm retaining wall may be functionally equivalent to an apparatus having two 100 µm, aligned retaining walls.

Additionally, in some instances, the height of the channel is 1.5 to 4 times, 2 to 3 times, or 1.75 to 3.5 times the height of the retaining wall. In some embodiments, the channel opening defined by the top substrate layer, the bottom substrate layer, and the retaining wall may be about ⅓ to ½ the height of the channel. In some cases, the width of the channel is 1.5 to 4 times, 2 to 3 times, or 1.75 to 3.5 times a height of the retaining wall. In some embodiments, the channel opening defined by the top substrate layer, the bottom substrate layer, and the retaining wall or walls may be about ⅓ to ½ the width of the channel. Further, in some embodiments, the height of the channel is 1.5 to 3 times a diameter of the nerve. In some cases, the width of the channel is 1.5 to 3 times a diameter of the nerve. Moreover, in some instances, the height of the channel and the width of the channel are substantially equal. Channel height and width may be adjusted independently, but in many cases have similar dimensions. However, the channel cross-section need not be square. Any channel cross-section (square, trapezoidal, rectangular, round, ovoid, etc.) may be used.

The apparatus of FIG. 1A also includes a plurality of electrodes (160) disposed on interior surfaces (111, 121) of the channel (130). As depicted in FIGS. 1A and 1B, the interior surfaces (111, 121) are interior surfaces of recesses (112, 122) in the top substrate layer (110) and the bottom substrate layer (120). In particular, the interior surface (111) is an interior surface of the first recess (112) in the top substrate layer (110), and the interior surface (121) is an interior surface of the second recess (122) in the bottom substrate layer (120). Thus, in some embodiments, top electrodes are disposed on the surface of the recess of the top surface layer and bottom electrodes are disposed on the surface of the recess of the bottom substrate layer. Additionally, as illustrated in FIG. 1A, the plurality of electrodes (160) are substantially parallel to one another and are oriented substantially perpendicular to a length of the channel (130). However, other arrangements of electrodes are also possible. Moreover, in some cases, the top electrodes of an apparatus are aligned with the bottom electrodes in an x-direction and/or in a y-direction, where the xy-plane can refer to the plane of an interior surface of the channel on which the electrodes are disposed (such that, for example, the x-direction corresponds to the L-direction in FIG. 1A). Further, in some embodiments, a height of the channel (as described above) is defined by a distance, such as a shortest distance, in the z-direction between the top electrodes and the bottom electrodes, wherein the z-direction is understood to be orthogonal to the xy-plane. Electrodes configured in a manner described herein can be operable to detect an electrical signal transmitted by the nerve along a length of the nerve, in particular a length of the nerve corresponding to the L-direction in FIG. 1A. In addition, as described further herein, the retaining wall of an apparatus described herein can retain the nerve in contact with one or more of the electrodes, including when the electrodes have a configuration described hereinabove.

Further, electrodes having an arrangement described herein, such as a longitudinal arrangement of electrodes along the channel length, can provide a means of determining the type of nerve disposed in the channel. As understood by a person of ordinary skill in the art, nerves transmit electrical signals or electrical impulse along a length of the nerve. The known distance between electrodes can thus be correlated with time series data of electrical recordings to estimate conduction velocity along the length of the nerve. Differing nerve fiber types such as alpha motor neuron and group A, B, or C nerve fibers can be classified by conduction velocity. As the signal is transmitted, it will cross each electrode in the plurality of electrodes at a slightly different time, permitting detection of the velocity and intensity of the electrical signal. Further, detecting electrical signals along the same nerve over a period of time (such as a period of time of up to 1 month or greater than 1 month) may be used to monitor the nerve's health and condition over time.

Figure 3A:
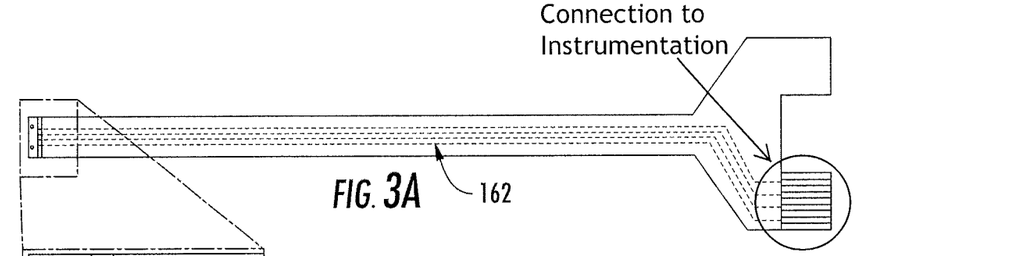
FIG. 3A illustrates a top plan view of an apparatus according to one embodiment described herein.
Figure 3B:
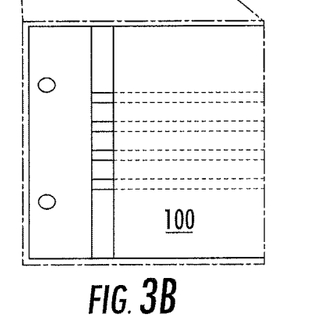
FIG. 3B illustrates an enlarged view of a portion of the apparatus of FIG. 3A.
Figure 3C:
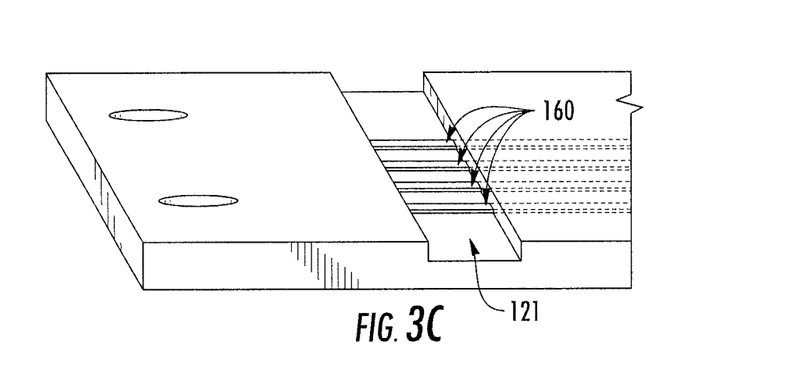
FIG. 3C illustrates a perspective view of a portion of the apparatus of FIG. 3A.

An apparatus described herein may also include one or more electrical interconnects coupling electrodes of the apparatus to an additional component of the apparatus or to an external device, such as a power supply, detector, and/or controller. Such electrical interconnects are illustrated in FIG. 3. FIG. 3A illustrates a top plan view of an apparatus according to one embodiment described herein. FIG. 3B illustrates an enlarged view of a portion of the apparatus of FIG. 3A. FIG. 3C illustrates a perspective view of this same portion of the apparatus. With reference to FIG. 3, electrical interconnects (162) conduct electrical signals between the plurality of electrodes (160) and additional electrical instrumentation (not shown).

Turning again to details of specific components of apparatuses described herein, apparatuses described herein comprise top and bottom substrate layers. The top substrate layer and the bottom substrate layer may be formed from any material not inconsistent with the objectives of the invention. For example, in some cases, the top substrate layer and the bottom substrate layer may be formed from, comprise, consist of, or consist essentially of a flexible material, including a flexible biocompatible polymer. Flexibility of the top substrate layer and the bottom substrate layer may facilitate insertion of the nerve into the channel of the apparatus, allowing for ease of manipulation of the apparatus for placement on the nerve and then for subsequent removal from the nerve. Further, it is to be understood that a "flexible" substrate layer can be elastically or reversibly bent or flexed, without breaking or permanent deformation, from a planar position to a non-planar position through at least 15 degrees, at least 20 degrees, at least 30 degrees, or at least 45 degrees. In some instances, a flexible substrate layer can be flexed or bent through 10-45, 10-30, 15-45, 15-30, 20-45, or 20-30 degrees without breaking or permanently deforming. In some embodiments, the top and/or bottom substrate layer is formed from a polyimide, parylene, a silicone, a polyurethane, or a combination thereof. In some cases, the top and/or bottom substrate layer is formed from poly (4,4'-oxydiphenylene-pyromellitimide), which may be referred to by the trade name KAPTON. Additionally, the top substrate layer and the bottom substrate layer of an apparatus described herein may be fabricated or formed from the same materials, and may have the same or similar shapes and/or sizes. However, the top substrate layer and the bottom substrate layer may also be formed from different materials, and may have dissimilar shapes and sizes.

Further, in some embodiments, the top substrate layer and/or the bottom substrate layer is substantially transparent to light of wavelengths from 400 nm to 700 nm. When the top substrate layer and/or the bottom substrate layer are substantially transparent, visual inspection can determine if there is a nerve in the channel of the apparatus. The substantially transparent top substrate layer and/or the substantially transparent bottom substrate layer can transmit at least 60%, at least 70%, at least 80%, at least 85%, at least 90%, at least 95%, or at least 99% of visible light having wavelengths from 400 nm to 700 nm, from 425 nm to 675 nm, or from 450 nm to 650 nm.

Apparatuses described herein, in some cases, also comprise a spacer layer. The spacer layer may comprise or be formed from any material not inconsistent with the objectives of the present invention, including a material described hereinabove for the top and bottom substrate layers. In some embodiments, the spacer layer may comprise, consist, or consist essentially of a polyimide film with a thermosetting acrylate adhesive film. Additionally, the spacer layer may comprise electronic components such as a miniature wireless module or electrical stimulator circuitry.

Further, a top substrate layer, a bottom substrate layer, and/or a spacer layer of an apparatus described herein may be coated or surface treated to improve the biocompatibility of the apparatus or to reduce inflammation near the apparatus. Any coating not inconsistent with the objectives of the present invention may be used. Coating materials may include, but are not limited to, controlled-release drugs, polyethylene glycol, biomolecules such as proteins, peptides, amino acids, nucleic acids, antibodies or aptamers, or growth factors such as neural growth factor, brain derived growth factor, or any neurotrophins.

In addition, apparatuses described herein comprise electrodes and/or additional electrical interconnects. The electrodes and/or electrical interconnects may be formed from any electrically conductive material not inconsistent with the objectives of the present invention. In some cases, for example, the electrodes comprise, consist of, consist essentially of, or are formed from an inorganic material such as a metal or metal oxide, which may include platinum, copper, gold, or iridium oxide. Electrodes and/or interconnects may also be formed from an organic material such as poly(3,4-ethylenedioxythiophene), polypyrrole, carbon nanotubes, graphene, or a combination thereof. The electrical impedance and charge storage capacity of the electrodes may also have any values not inconsistent with the objectives of the present disclosure. Moreover, the foregoing values may be selected based in part on the exposed area of the electrodes. In some cases, the exposed area of the electrodes can be varied by changing the width of each electrode or by changing the width of the channel in which the electrodes are disposed. In some implementations, the electrodes may be insulated except where they are exposed in the channel. Further, in some cases, the thickness of the insulation corresponds to the retaining wall height. Moreover, any desired number of electrodes may be disposed in a channel of an apparatus described herein. In some embodiments, the number of electrodes ranges from 1 to 64, 2 to 32, or 4 to 20 electrodes. Other numbers of electrodes may also be used.

In addition, in some cases, the flexible nature of the top substrate layer and/or the bottom substrate layer may result in cracking or delamination of an electrode material from the substrate during bending and stretching of the apparatus. In some such embodiments, this difficulty may be overcome by patterning electrode materials in a serpentine pattern to accommodate torsion due to both in plane and out of plane bending. In other embodiments, liquid metal interconnects encapsulated within microfluidic channels may be used to prevent breaking and electrical shorts due to torsion.

It is to be understood that apparatuses described herein can have any combination of features, components, or properties described hereinabove not inconsistent with the objectives of the present invention.

II. Methods of Nerve Stimulation and/or Monitoring

In another aspect, methods of stimulating and/or monitoring a nerve are described herein. In some implementations, such a method comprises placing a nerve in the channel of an apparatus described hereinabove in Section I. Any apparatus described hereinabove in Section I may be used. For example, the apparatus can comprise a top substrate layer, a bottom substrate layer in facing opposition to the top substrate layer, and a channel disposed between the top substrate layer and the bottom substrate layer. The apparatus can further comprise a plurality of electrodes disposed on one or more interior surfaces of the channel. Additionally, the channel is defined by the top substrate layer, the bottom substrate layer, and a retaining wall extending at least partially between the top substrate layer and the bottom substrate layer. The retaining wall retains the nerve within the channel. Moreover, placing the nerve in the channel of the apparatus comprises placing the nerve in contact with the plurality of electrodes. The method further comprises sending electrical signals from the electrodes to the nerve and/or receiving electrical signals from the nerve to the electrodes.

In addition, in some cases, the top substrate layer and the bottom substrate layer of the apparatus define an opening of the channel at a proximal end of the apparatus, and placing the nerve in the channel of the apparatus comprises first flexing an end of the top substrate layer away from a corresponding end of the bottom substrate layer to increase the size of the opening of the channel, and subsequently placing the nerve in the channel through the opening of the channel. A method described herein may also comprise joining the top substrate layer and the bottom substrate layer to close the opening of the channel at the proximal end of the apparatus.

As described further herein, the nerve placed in the channel of the apparatus can be an intact or non-severed nerve. Additionally, a method described herein can be carried out without penetrating the nerve within the channel of the apparatus. Moreover, in some cases, the nerve is a nerve of a living patient, and the method further comprises placing the apparatus within a biological compartment of the patient. The biological compartment can be an interior region of the patient's body. A method described herein may also comprise sealing the apparatus within the biological compartment of the patient after placing the nerve in the channel of the apparatus, including by sealing or closing the biological compartment, such as by using sutures or staples. In addition, in some cases, the apparatus is not permanently implanted within the patient, but may instead be removed from the patient following a desired or therapeutic time period. Such an apparatus may accordingly not be solubilized, degraded, or otherwise decomposed in situ, but may instead be removed from the patient intact after a desired time period. In some implementations, the apparatus may be left in the body of the patient for up to a week, a month, a year, a decade, several decades, or many decades. Further, it is generally to be understood that the nerve may not grow into or become physically attached to the apparatus while the apparatus is disposed in the biological compartment, other than being retained within the channel in a manner described herein. Moreover, in some embodiments, removing the apparatus from the patient after a period of time does not damage the nerve. Thus, in some cases, a method described herein further comprises removing the apparatus from the patient after sealing the apparatus within the biological compartment of the patient, and removing the nerve from the apparatus, both without damaging or severing the nerve.

Additionally, in some embodiments, a method described herein further comprises sending and/or receiving electrical signals to and/or from the nerve, including while the nerve is disposed within a channel of an apparatus described herein. Such electrical signals can be sent from and/or received by electrodes of the apparatus. Further, electrical signals exchanged between a nerve and an apparatus can be used to stimulate, monitor, and/or characterize the nerve. For example, in some instances, a method described herein comprises sending electrical signals from electrodes of an apparatus to the nerve disposed in a channel of the apparatus, thereby stimulating the nerve. Electrical signals can be sent to the nerve a plurality of times, including in a temporally periodic, regular, or irregular manner. In other implementations, a method comprises receiving electrical signals with electrodes of an apparatus from a nerve disposed in contact with the electrodes within a channel of the apparatus. As in the case of sending electrical signals, electrical signals may also be received by the electrodes a plurality of times or over a desired period of time. Further, in some embodiments, a method described herein comprises measuring the velocity and/or intensity of an electrical signal or series of electrical signals received from a nerve, including as a function of time and/or distance along the length of the nerve. Moreover, in some cases, comparing time series data between two electrode sites to calculate conduction velocity can be used to identify or distinguish different nerve fiber types, such as sensory or motor neurons.

More generally, methods described herein can be useful for electrical stimulation of a peripheral nerve intended to cause a physiological response or to provide therapy to the nerve. In addition, methods described herein can be useful for the diagnosis of conditions by combinations of electrical stimulation, recording of neural activity, and monitoring changes of other biometrics caused by stimulation. Further, some methods can provide electrical stimulation intended to mimic sensory perception such as touch feedback from a prosthetic device. Further still, some methods described herein can be useful for monitoring either endogenous or stimulated neural activity for the purpose of determining appropriate electrical stimulation to be delivered through an apparatus described herein either manually or by a feedback control mechanism. In addition, methods described herein can be useful for recording neural activity to be used as a control signal for driving prosthetics or any other electronic or mechanical device.

Specific steps of methods according to the present disclosure will now be further described with reference to the figures. It is to be understood that the same reference numerals used in differing figures generally correspond to the same steps of a method or features of an apparatus.

Figure 4A:
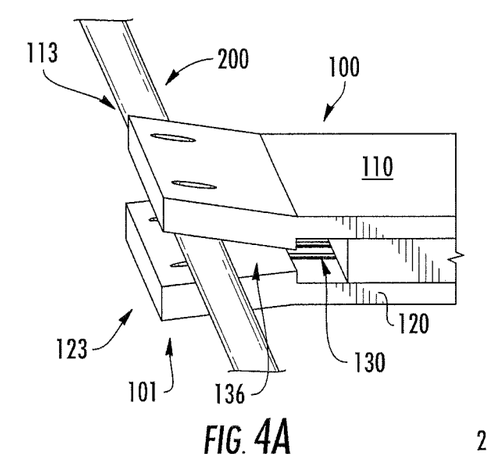
FIGS. 4A-4C each illustrates a step of a method according to one embodiment described herein.
Figure 4B:
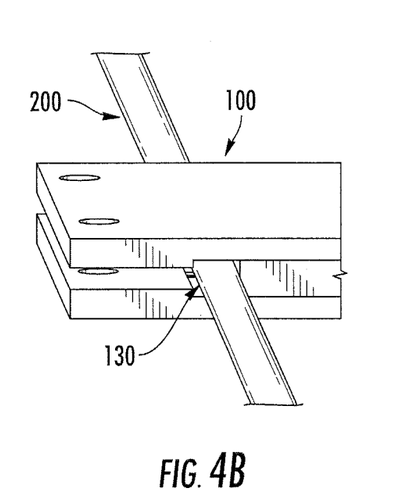
Figure 4C:
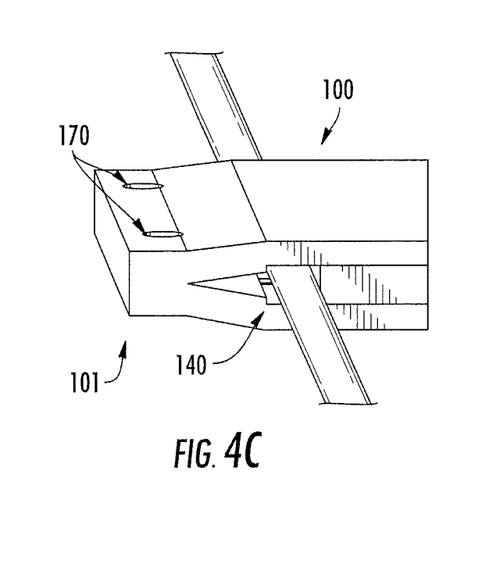

FIGS. 4A-4C each illustrates a step of a method according to one embodiment described herein. As illustrated in FIGS. 4A-4C, a top substrate layer (110) and a bottom substrate layer (120) of an apparatus (100) together define an opening (136) of a channel (130) of the apparatus (100) at a proximal end (101) of the apparatus (100). The method depicted in FIGS. 4A-4C comprises placing a nerve (200) in the channel (130) of the apparatus (100). Specifically, to place the nerve (200) within the channel (130), an end (113) of the top substrate layer (110) is flexed or bent away from a corresponding end (123) of the bottom substrate layer (120) in order to increase the size of the opening (136). The nerve (200) is then placed in the channel (130) laterally or sideways through the opening (136) of the apparatus (100). The flexed or bent ends (113, 123) of the top and bottom substrate layers (110, 120) are depicted in FIG. 4A. Additionally, as illustrated in FIG. 4A, the nerve (200) has already been inserted into the channel (130) following flexing of the ends (113, 123) of the top and bottom substrate layers (110, 120). As illustrated in FIG. 4B, the ends (113, 123) of the top and bottom substrate layers (110, 120) have been moved back to their original planar or unflexed position following insertion of the nerve (200) into the channel (130).

In the step illustrated in FIG. 4C, the top substrate layer (110) and the bottom substrate layer (120) have been joined or attached to one another to close the opening (136) of the channel (130) at the proximal end (101) of the apparatus (100), following insertion of the nerve (200). The top substrate layer (110) and the bottom substrate layer (120) may be joined in any manner not inconsistent with the objectives of this invention. For example, closing or joining may be accomplished with a mechanical interlocking mechanism, staples, clamps, or sutures (not shown). Moreover, the top substrate layer (110) and/or the bottom substrate layer (120) may include closure guidance markings, indentations, or holes (170). Such closure guidance markings (170) can be used to align the top and bottom substrate layers (110, 120) and to facilitate accurate and efficient closing of the opening (136). However, it is again to be understood that closing the opening (136) as described above is optional and may provide only secondary containment or retention of the nerve (200) within the channel (130). The retaining wall (140) may serve as the primary means of retaining the nerve (200) within the channel (130).

Further, although not illustrated in FIG. 4, it is to be understood that the nerve (200) may be removed from the channel (130) of the apparatus (100) by sliding or otherwise moving the nerve (200) past the retaining wall (140) and through the opening (136) after the first and second substrate layers (110, 120) are detached or unjoined from one another. The first and second substrate layers (110, 120) may also be flexed open following detaching or unjoining of the layers (110, 120) from one another.

Figure 5:
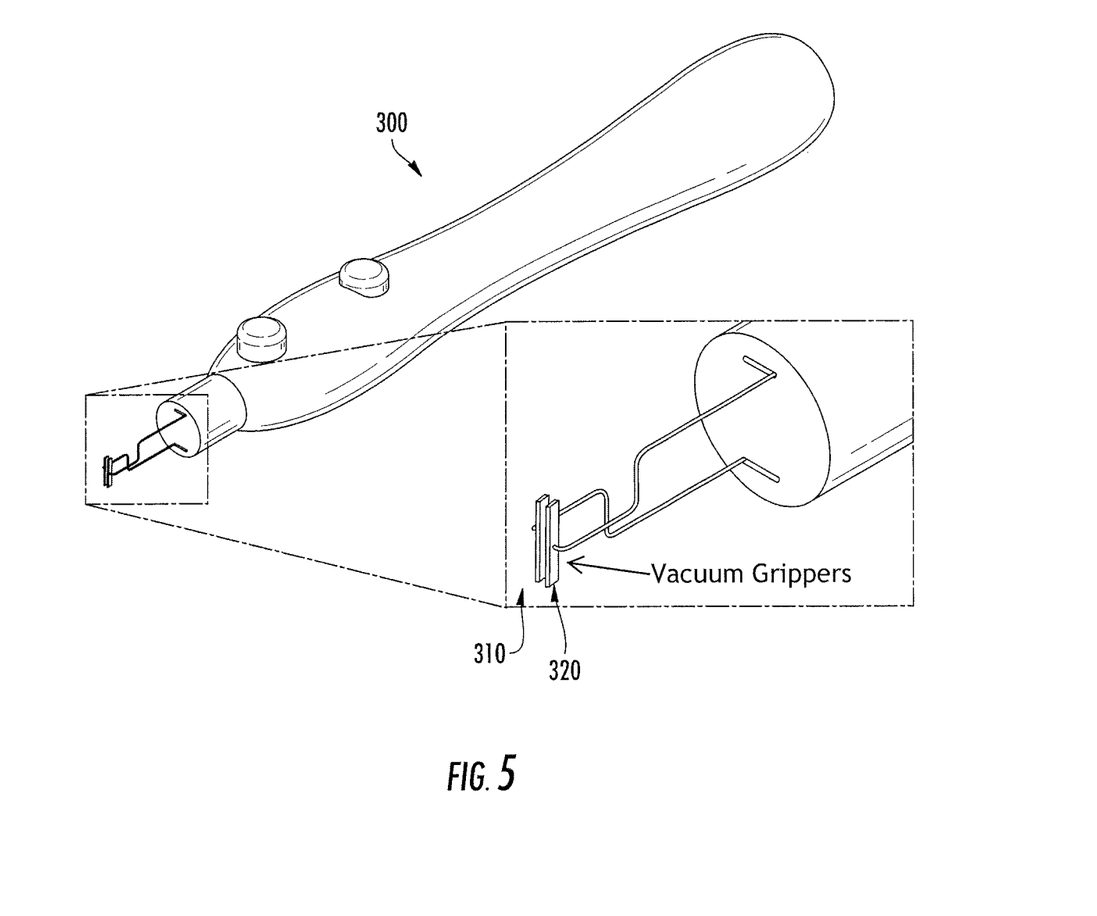
FIG. 5 illustrates a perspective view of a tool used to perform steps of a method according to some embodiments described herein.
Figure 6A:
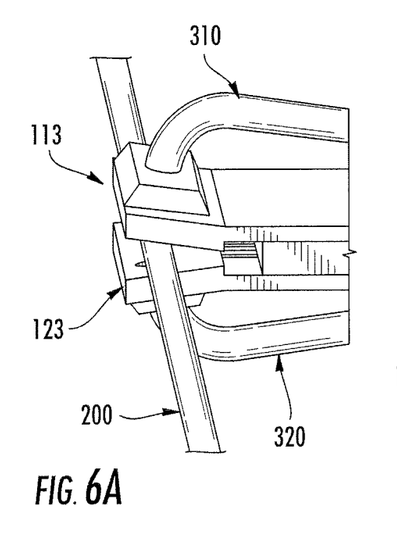
FIGS. 6A-6D each illustrates a step of a method according to one embodiment described herein.
Figure 6B:
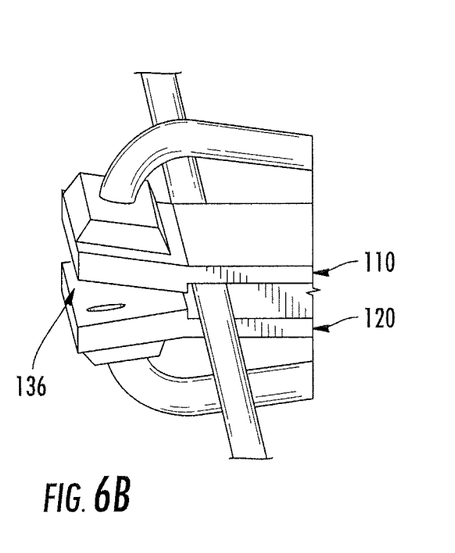
Figure 6C:
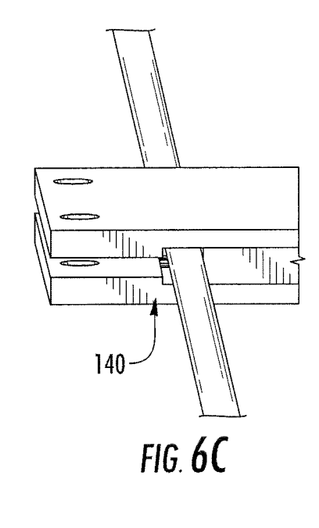
Figure 6D:
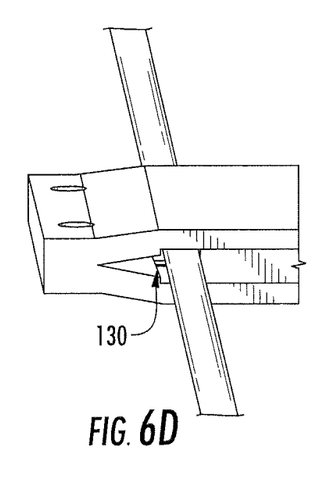

In addition, in some implementations, a vacuum tool may be used to carry out one or more of the steps illustrated in FIGS. 4A-4C. FIG. 5 illustrates a perspective view of such a tool, and FIGS. 6A-6D illustrate the use of the tool of FIG. 5 in steps of a method similar to the steps depicted in FIGS. 4A-4C. As depicted in FIG. 5, a vacuum tool (300) comprises a first vacuum gripper (310) and a second vacuum gripper (320) in facing opposition to one another. As illustrated in FIGS. 6A-6D, the vacuum grippers (310, 320) can be applied to the top substrate layer (110) and to the bottom substrate layer (120), and a vacuum can be applied to bend or pull back the ends (113, 123) of the first and second layers (110, 120) to widen the opening (136) of the channel (130) for insertion of the nerve (200). In FIG. 6A, the nerve (200) is partially inserted, while in FIG. 6B the nerve (200) is fully inserted into the channel (130).

It is to be understood that methods described herein can include any combination of steps and/or any combination of apparatus features, components, or properties described hereinabove not inconsistent with the objectives of the present invention.

Example 1

Apparatus for Nerve Stimulation and/or Monitoring

Figure 7:
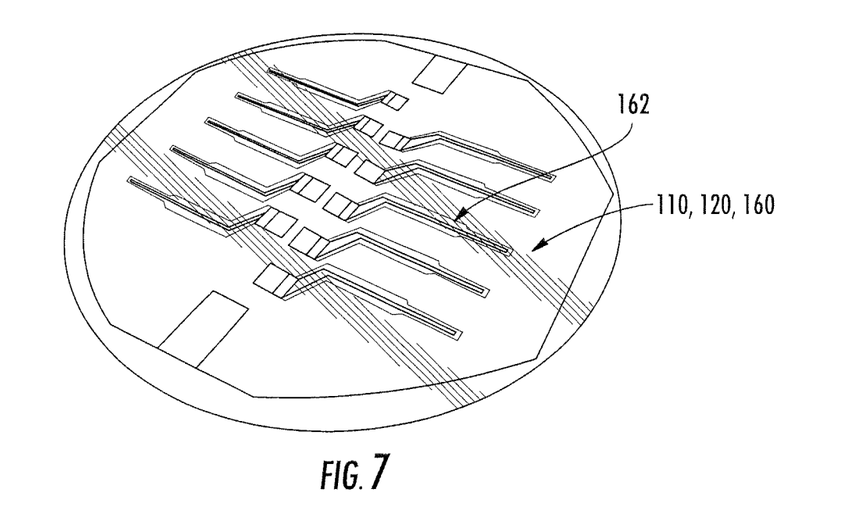
FIG. 7 illustrates a perspective view of portions of apparatuses according to one embodiment described herein.

An apparatus for nerve stimulation and/or monitoring according to one embodiment described herein was prepared as follows. A top substrate layer having electrodes and a bottom substrate layer having electrodes were made using conventional microfabrication methods, including photolithographic patterning and sputter deposition of thin films. Specifically, to form a substrate layer, a pre-fabricated substrate formed from a KAPTON polyimide film (thickness=75 μm) was mounted on a silicon wafer for processing. A metal pattern forming the electrodes and metal interconnects was then deposited using platinum as the metal. A spinnable polyimide solution was next applied to achieve a desired recess depth, followed by selective etching to expose the metal electrodes along the channel. Finally, the polyimide film was cured in a nitrogen environment. FIG. 7 is a photograph of ten copies of a coated substrate layer (110 and/or 120) with a plurality of electrodes (160) and interconnects (162). The substrate layers were separated by cutting the desired layer outline using a laser cutting/engraving tool.

Figure 8:
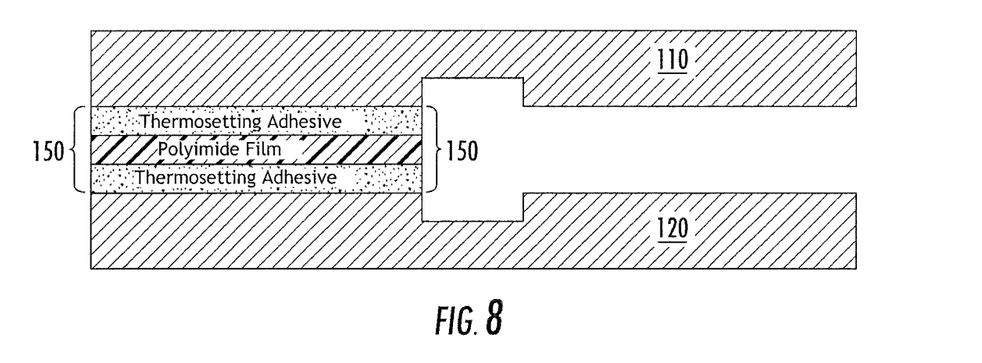
FIG. 8 illustrates a sectional view of an apparatus according to one embodiment described herein.

A spacer layer (150) was fabricated from an alternating stack of polyimide film and thermosetting polymer to achieve a desired total thickness of the spacer layer (150), as shown in FIG. 8. The dry stack was then cut to the desired length and width to form a spacer layer that could be disposed between a top substrate layer and a bottom substrate layer fabricated as described above. In particular, the spacer layer was permanently bonded to the top substrate layer and to the bottom substrate layer using a Flip-Chip-Bonding system to allow precise alignment, pressure control, and multi-stage temperature control.

An apparatus described herein may also be formed by depositing electrode material or otherwise forming electrodes or metal contacts on a substrate, such as a silicon wafer, followed by applying or forming a polyimide film over the functional substrate. In particular, a polyimide solution can be spun on the substrate. In one approach, after spinning the polyimide, the substrate is soft baked to evaporate solvents. Using a photoresist mask, selective wet or dry etching is used to expose the metal pads/contacts/electrodes and to define the channel of the apparatus, lined with electrodes. The polyimide is then further cured in a nitrogen environment to complete the apparatus.

In a second approach, after spinning the polyimide, the substrate is soft baked to evaporate solvents. Photodefinable polyimide is then patterned using a photomask and standard lithography processing. After photolithography patterning and development, the polyimide is then further cured in a nitrogen environment. Finally, a plasma etching process is used to remove residual polyimide from the patterned channel and fully expose the electrode surfaces.

Example 2

Method for Nerve Stimulation and/or Monitoring

Figure 9A:
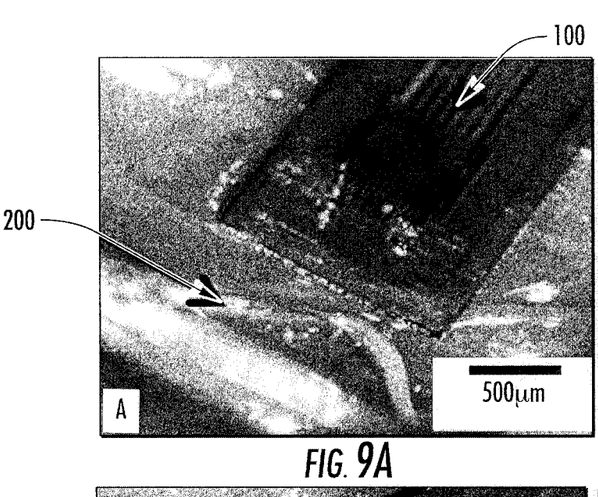
FIGS. 9A-9D each illustrates a step of a method according to one embodiment described herein.
Figure 9B:
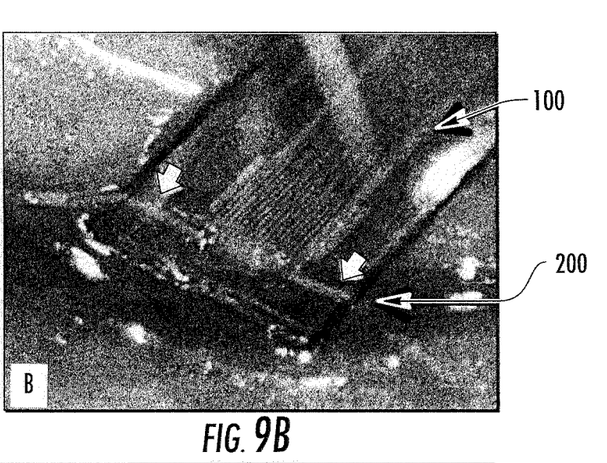
Figure 9C:
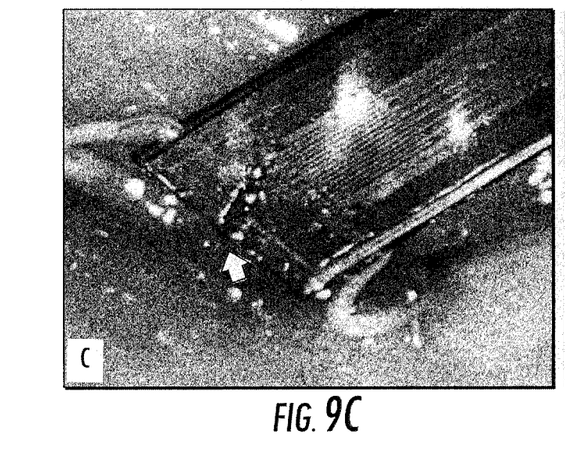
Figure 9D:
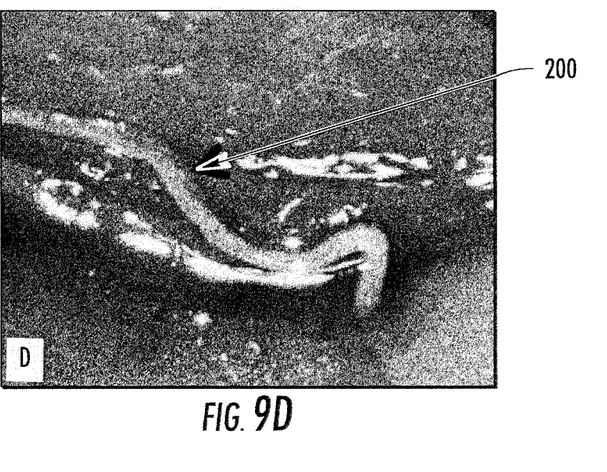

A method for stimulating and/or monitoring a nerve according to one embodiment described herein was carried out as follows. The apparatus of Example 1 was surgically placed on the isolated cutaneous branch of the sciatic nerve of an anesthetized rat. The nerve was specifically placed in the channel of the apparatus in contact with the plurality of electrodes, and 9-0 sutures were inserted through the closure guidance holes to "close" the channel by joining the proximal ends of the top substrate layer and the bottom substrate layer. An electrical signal was then sent from the electrodes to the nerve. The nerve was then removed from the apparatus without causing damage to the nerve, and the apparatus was then removed from the rat. FIGS. 9A-9D illustrate this process. Specifically, FIG. 9A illustrates the apparatus (100) and the nerve (200) prior to placement of the nerve (200) within the apparatus (100). FIG. 9B illustrates the nerve (200) within the apparatus (100). FIG. 9C illustrates the appearance of the biological compartment during electrical stimulation of the nerve. FIG. 9D illustrates the nerve (200) in the biological compartment following removal of the nerve (200) from the apparatus (100), and the removal of the apparatus (100) from the biological compartment.

Various implementations of the disclosure have been described in fulfillment of the various objectives of the disclosure. It should be recognized that these implementations are merely illustrative of the principles of the present disclosure. Numerous modifications and adaptations thereof will be readily apparent to those skilled in the art without departing from the spirit and scope of the disclosure.

The invention claimed is:

1. An apparatus for nerve stimulation and/or monitoring comprising:
   a top substrate layer;
   a bottom substrate layer in facing opposition to the top substrate layer;
   a channel disposed between the top substrate layer and the bottom substrate layer; and
   a plurality of electrodes disposed on one or more interior surfaces of the channel,
   wherein the channel is defined by the top substrate layer, the bottom substrate layer, and one or more retaining walls extending at least partially between the top substrate layer and the bottom substrate layer;
   wherein the one or more retaining walls extends substantially normally from the top substrate layer and/or from the bottom substrate layer to define the channel; and
   wherein the one or more retaining walls is configured to retain the nerve within the channel.

2. The apparatus of claim 1 further comprising a spacer layer disposed between the top substrate layer and the bottom substrate layer.

3. The apparatus of claim 1, wherein the top substrate layer and the bottom substrate layer define an opening of the channel at a proximal end of the apparatus.

4. The apparatus of claim 1, wherein the top substrate layer and the bottom substrate layer are formed from a flexible material.

5. The apparatus of claim 1, wherein the top substrate layer and the bottom substrate layer are formed from a biocompatible polymer comprising one or more of a polyimide, parylene, a silicone, and a polyurethane.

6. The apparatus of claim 1, wherein the top substrate layer and the bottom substrate layer are substantially transparent to light of wavelengths from 400 nm to 700 nm.

7. The apparatus of claim 1, wherein the electrodes are formed from one or more of platinum, poly(3,4-ethylenedioxythiophene), polypyrrole, carbon nanotubes, graphene, and iridium oxide.

8. The apparatus of claim 1, wherein a height and/or a width of the channel is up to 1000 µm.

9. The apparatus of claim 1, wherein a height of at least one of the one or more retaining walls is up to 300 µm.

10. The apparatus of claim 1, wherein a height and/or a width of the channel is 1.5 to 4 times a height of at least one of the one or more retaining walls.

11. The apparatus of claim 1, wherein a height of the channel and a width of the channel are substantially equal.

12. The apparatus of claim 1, wherein a height of the channel is 1.5 to 3 times a diameter of the nerve.

13. The apparatus of claim 1, wherein the one or more retaining walls is configured to retain the nerve in contact with the electrodes.

14. The apparatus of claim 1, wherein the plurality of electrodes are substantially parallel to one another and are oriented substantially perpendicular to a length of the channel.

15. The apparatus of claim 1, wherein the top substrate layer comprises a recess and the bottom substrate layer comprises a recess.

16. The apparatus of claim 15, wherein:
   the channel is defined by the recess of the top substrate layer, the recess of the bottom substrate layer, and the one or more retaining walls; and
   the plurality of electrodes are disposed on a surface of the recess of the top substrate layer and/or on a surface of the recess of the bottom substrate layer.

17. The apparatus of claim 1, wherein the apparatus is configured to be non-penetrating to the nerve.

18. A method of stimulating and/or monitoring a nerve comprising:
   placing the nerve in the channel of the apparatus of claim 1 in contact with the plurality of electrodes; and
   sending electrical signals from the electrodes to the nerve and/or receiving electrical signals from the nerve to the electrodes.

19. The method of claim 18, wherein:
   the top substrate layer and the bottom substrate layer of the apparatus define an opening of the channel at a proximal end of the apparatus;
   placing the nerve in the channel of the apparatus comprises:
      flexing an end of the top substrate layer away from a corresponding end of the bottom substrate layer to increase the size of the opening of the channel; and
      placing the nerve in the channel through the opening of the channel; and
   the method further comprises joining the top substrate layer and the bottom substrate layer to close the opening of the channel at the proximal end of the apparatus.

20. The method of claim 18, wherein the nerve is an intact nerve and the apparatus does not penetrate the nerve.

* * * * *